(12) United States Patent
Chewter et al.

(10) Patent No.: US 8,696,999 B2
(45) Date of Patent: Apr. 15, 2014

(54) RISER REACTOR SYSTEM AND A PROCESS FOR THE PREPARATION OF AN OLEFINIC PRODUCT

(75) Inventors: Leslie Andrew Chewter, Amsterdam (NL); Hubertus Wilhelmus Albertus Dries, Amsterdam (NL); Rene Samson, Amsterdam (NL); Mao Ye, Amsterdam (NL)

(73) Assignee: Shell Oil Company, Houston, TX (US)

( * ) Notice: Subject to any disclaimer, the term of this patent is extended or adjusted under 35 U.S.C. 154(b) by 184 days.

(21) Appl. No.: 13/140,967

(22) PCT Filed: Dec. 21, 2009

(86) PCT No.: PCT/EP2009/067675
§ 371 (c)(1),
(2), (4) Date: Aug. 24, 2011

(87) PCT Pub. No.: WO2010/072730
PCT Pub. Date: Jul. 1, 2010

(65) Prior Publication Data
US 2011/0306814 A1   Dec. 15, 2011

(30) Foreign Application Priority Data

Dec. 22, 2008  (EP) ..................................... 08172533

(51) Int. Cl.
*B01J 8/08*  (2006.01)
*B01J 8/18*  (2006.01)

(52) U.S. Cl.
USPC ............................. 422/214; 422/139; 422/145

(58) Field of Classification Search
USPC .......................................... 422/139, 145, 214
See application file for complete search history.

(56) References Cited

U.S. PATENT DOCUMENTS

| | | | | | |
|---|---|---|---|---|---|
| 4,071,573 | A | * | 1/1978 | Owen et al. | 585/402 |
| 4,753,780 | A | * | 6/1988 | Bowen | 422/214 |
| 4,875,994 | A | * | 10/1989 | Haddad et al. | 208/113 |
| 6,596,242 | B1 | * | 7/2003 | Dries | 422/139 |

* cited by examiner

*Primary Examiner* — Lessanework Seifu (57) ABSTRACT

A riser reactor system comprising a riser reactor and a catalyst feed device for fluidized catalyst, the riser reactor having a riser interior in which catalyst is flowing during normal operation, and the feed device comprising an annular trough surrounding the riser interior, the annular trough having an upstream opening for receiving fluidized catalyst, and at least one substantially circumferential downstream opening providing fluid communication between the trough and the riser interior; and a process for the preparation of an olefinic product using a riser reactor system as claimed in any one of the preceding claims, the process comprising reacting an oxygenate feedstock in the presence of an oxygenate conversion catalyst under oxygenate-to-olefin conversion conditions in the riser reactor system, to obtain the olefinic product.

10 Claims, 3 Drawing Sheets

RISER REACTOR SYSTEM AND A PROCESS FOR THE PREPARATION OF AN OLEFINIC PRODUCT

PRIORITY CLAIM

The present application claims priority from PCT/EP2009/067675, filed 21 Dec. 2009, which claims priority from European Application EP 08172533.5, filed 22 Dec. 2008.

BACKGROUND

This invention relates to a riser reactor system comprising a catalyst feed device and a process for the preparation of an olefinic product.

Processes for the preparation of olefins from oxygenates are known in the art. Of particular interest is often the production of light olefins, in particular ethylene and/or propylene. The oxygenate feedstock can for example comprise methanol and/or dimethylether, and an interesting route includes their production from synthesis gas derived from e.g. natural gas or via coal gasification.

For example, WO2007/135052 discloses a process wherein an alcohol and/or ether containing oxygenate feedstock and an olefinic co-feed are reacted in the presence of a zeolite having one-dimensional 10-membered ring channels to prepare an olefinic reaction mixture, and wherein part of the obtained olefinic reaction mixture is recycled as olefinic co-feed. With a methanol and/or dimethylether containing feedstock, and an olefinic co-feed comprising C4 and/or C5 olefins, an olefinic product rich in light olefins can be obtained.

Another oxygenate-to-olefins process is described in WO 2004/037950 A1, wherein an oxygenate feedstock is converted in a riser reactor system having a plurality of parallel risers.

Yet another process for the conversion of oxygenate into olefins is described in WO 01/62689, wherein oxygenate is stagewise injected into a fluidized bed reaction zone.

Moreover it has been shown in International patent applications No. PCT/EP2008/065863 and PCT/EP2008/065872 (both unpublished at the date of filing the present application, and both incorporated herein by reference) that and how oxygenate-to-olefins processes can benefit from staged feeding of the oxygenate feed. In a riser reactor system it is moreover preferable to add catalyst as well.

Applicants have realized that it can be beneficial to stage feed admission in a riser reactor system by adding feed at various heights. However, there seems to be no suitable catalyst inlet device available for this task that allows suitable admission of catalyst into a riser reactor system. At an elevated position in a riser, a flow pattern has developed and should desirably not be significantly disturbed by the addition of further catalyst. The problem is particularly pronounced when it is desired to use a riser reactor system of significant diameter, such as of larger than 0.5 m, larger than 1 m, or even more. A riser reactor as disclosed in U.S. Pat. No. 4,927,522 for a fluidized catalytic cracking (FCC) system does not address these problems. In the known reactor, catalyst is added simply from a side inlet to the riser. The inventors of the present invention have realized that this biases the catalyst towards one side of the reactor and severely disturbs an already existing flow pattern in the reactor.

There is a need for an improved catalyst feed device for riser reactor systems.

SUMMARY OF THE INVENTION

According to the first aspect of the invention there is provided a riser reactor system comprising a riser reactor and a catalyst feed device for fluidized catalyst, the riser reactor having a riser interior in which catalyst is flowing during normal operation, and the feed device comprising an annular trough surrounding the riser interior, the annular trough having an upstream opening for receiving fluidized catalyst, and at least one substantially circumferential downstream opening providing fluid communication between the trough and the riser interior.

DETAILED DESCRIPTION OF THE INVENTION

The inventors of the present invention have found that the introduction of fluidised catalyst is preferably introduced around the circumference of the riser rather than from a simple side inlet. An annular trough is understood herein to be a trough surrounding the circumference of the riser, whatever the cross-sectional shape of the riser may be, and also the annular trough does not need to be circular.

Thus in use, introduction of fluidised catalyst through the feed device for certain embodiments of the invention result in a number of different benefits: the fluidised catalyst may be added more evenly around the circumference of the riser, thus distributing the catalyst more evenly around the reactor, and any flow already present in the riser reactor is less disturbed by the introduction of the fluidised catalyst.

Typically the annular trough surrounds a first portion of the riser interior and typically the opening provides fluid communication between the trough and a second portion of the riser interior. The first and second portions may be the same but are normally different.

For a further catalyst feed above a first catalyst inlet at the bottom of the riser, typically the catalyst feed device is at least 50 cm, preferably 75 cm, normally at least 1 m from the bottom of the riser reactor system.

In a preferred embodiment the at least one downstream opening is a substantially circumferential opening and typically an upper edge of an inner wall part defining the trough, functions as a weir over which fluid flows during use.

In another preferred embodiment, a plurality of downstream openings are arranged at various locations around the circumference of the riser.

One or more baffles may be provided in the trough, the baffle(s) being shaped or arranged to manipulate the flow of fluidised catalyst in the trough, for example to direct the fluidised catalyst over the weir. The baffles may be provided at any point around the circumference of the trough, however preferably at least one baffle is spaced away from said upstream opening, by between 10 to 170°, preferably 10 to 150°.

The catalyst feed device may comprise an annular shoulder typically less than 1 m above said trough, preferably less than 0.5 m above said trough, the shoulder extending inwards to an equal or greater extent than the inner wall defining the trough. An upper face of the shoulder normally tapers inwardly and downwardly.

Typically the trough comprises a gas inlet to further fluidise the fluidised catalyst.

In a simple embodiment of the riser reactor system, the riser reactor has a constant cross-sectional area.

The benefits of the catalyst feed device described herein increase for risers with larger cross-sectional areas. Preferably the inner cross-sectional area of the riser at or just upstream of the catalyst feed device can be 0.15 m$^2$ or more, in particular 0.5 m$^2$ or more, more in particular 1 m$^2$ or more, and can also be 2 m$^2$ or more. In this specification by way of example specific reference is made to circular risers; it will be understood however that other shapes such as e.g. square shape, are possible as well. For a circular riser, the inner diameter is suitably 0.5 m or more, in particular 1 m or more, more in particular 2 m or more.

In a preferred embodiment, the riser reactor system may comprise two or more serially arranged riser reactor stages, wherein each riser reactor stage comprises a single riser reactor segment or a plurality of parallel riser reactors.

The applicant has found that selectivity of an oxygenate conversion process towards lower olefins, in particular ethylene, can be significantly improved using a serial riser reactor system, in which fluidised catalyst is stagewise added to a plurality of the riser reactor stages, in particular to the first and at least one additional riser reactor stage.

Preferably therefore the riser reactor system comprises a further catalyst feed device, in particular wherein the further catalyst feed device is a catalyst feed device according to any one of the preceding claims. The further catalyst feed device is arranged at a different location along the length of the riser reactor system, such as at an upstream location or a downstream location. Preferably at least one catalyst feed device is provided for each riser reactor stage.

Preferably each riser reactor stage comprises a single riser reactor segment. Preferably therefore the riser reactor system comprises a plurality of riser segments.

In particularly preferred embodiments the riser reactor system comprises at least two co-linear riser segments where one is mounted on top of the other such that fluidised catalyst may flow up the lower riser segment and then continue up the upper riser segment and up any further riser segments thereabove.

Between 2 and 10, preferably between 2 and 5, more preferably three or four, riser reactor stages, such as riser segments, can be provided. In preferred embodiments, each riser reactor stage comprises a single segment of a riser reactor.

Preferably the first of the two or more serially arranged riser reactor stages has a smaller total cross-sectional area than at least one of the subsequent riser reactor stages. It is particularly beneficial if the total cross-sectional area of each subsequent riser reactor stage, after the first, is higher than that of the preceding riser reactor stage. The total cross-sectional area is the sum of the cross-sectional areas of all riser reactors in a particular stage. In preferred embodiments, when there is only one riser reactor segment in a stage, its cross-section defines the total cross-sectional area of that stage. Increasing the cross-sectional area can partly or fully compensate for the increase in volumetric flow rate due to additional catalyst (and optionally feedstock), so that the flow velocity in the riser does not increase beyond critical values impeding for example conversion, catalyst stability and/or attrition.

Thus for embodiments comprising at least two co-linear segments, typically the upper riser segment has a larger cross-sectional area than the lower riser segment. Indeed where the risers are circular in cross-section and so their cross-sectional area is proportional to the square of their diameter, an outer wall of the catalyst feed device may be a continuation of the wider diameter riser segment, and the inner wall of the catalyst feed device may be a continuation of the lower diameter riser segment.

The invention also provides a process for the preparation of an olefinic product within a riser reactor system as described herein, the process comprising reacting an oxygenate feedstock in the presence of an oxygenate conversion catalyst under oxygenate-to-olefin conversion conditions in the riser reactor system, to obtain the olefinic product.

Typically in use the oxygenate feedstock is contacted with an oxygenate conversion catalyst to obtain a riser reactor effluent from each stage and at least part, preferably substantially all, of the riser reactor effluent of a preceding riser reactor stage is fed into a subsequent riser reactor stage, and preferably fluidised catalyst and optionally oxygenate is added to a plurality of the riser reactor stages.

The riser reactor effluent of a preceding riser reactor stage comprises gaseous effluent and solid oxygenate conversion catalyst. Normally, at least 50 wt % of the gaseous effluent is fed to the subsequent riser reactor stage, in particular at least 80%, more in particular at least 90%. Further, it can be beneficial not to separate solids and gases between subsequent riser reactor stages. So, normally also at least 50 wt % of the solid oxygenate conversion catalyst is fed to the subsequent riser reactor stage, in particular at least 80%, more in particular at least 90%. More in particular, substantially all riser reactor effluent from one riser reactor stage can be fed to the subsequent riser reactor stage.

The oxygenate feedstock suitably comprises oxygenate species having an oxygen-bonded methyl group, such as methanol or dimethylether. Preferably the oxygenate feedstock comprises at least 50 wt % of methanol and/or dimethylether, more preferably at least 80 wt %, most preferably at least 90 wt %.

The oxygenate feedstock can be obtained from a different or separate reactor, which converts methanol at least partially into dimethylether and water. Water may be removed by e.g. distillation. In this way, less water is present in the process of converting oxygenate to olefins, which has advantages for the process design and lowers the severity of hydrothermal conditions the catalyst is exposed to.

The oxygenate feedstock can comprise an amount of water, preferably less than 10 wt %, more preferably less than 5 wt %. Preferably the oxygenate feedstock contains essentially no hydrocarbons other than oxygenates, i.e. less than 5 wt %, preferably less than 1 wt %.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

In one embodiment, oxygenate is added to each of the riser reactor stages. Preferably the oxygenate added at the different stages is derived from a common oxygenate feedstock source. The common oxygenate feedstock source can for example be a storage vessel, feed line, or a different or separate reactor. In this way oxygenate comprising feedstock of substantially the same composition is fed to and converted in each of the riser reactor stages.

In one embodiment, the mass flow rate of oxygenate conversion catalyst in each subsequent riser reactor stage, after the first, to which oxygenate is added is higher than in the preceding riser reactor stage. Thus, the addition of fresh oxygenate feed is accommodated by additional oxygenate conversion catalyst. In this way the weight hourly space velocity (WHSV), defined as the throughput of the weight of reactants and reaction products per hour, and per weight of catalyst in the reactor, can be maintained above a selected minimum value, in order to achieve sufficient conversion.

Preferably the oxygenate feedstock is reacted to produce the olefinic product in the presence of an olefinic co-feed. By an olefinic composition or stream, such as an olefinic product, product fraction, fraction, effluent, reaction effluent or the like is understood a composition or stream comprising one or more olefins, unless specifically indicated otherwise. Other species can be present as well. Apart from olefins, the olefinic co-feed may contain other hydrocarbon compounds, such as for example paraffinic compounds. Preferably the olefinic co-feed comprises an olefinic portion of more than 50 wt %, more preferably more than 60 wt %, still more preferably more than 70 wt %, which olefinic portion consists of olefin (s). The olefinic co-feed can also consist essentially of olefin (s).

Any non-olefinic compounds in the olefinic co-feed are preferably paraffinic compounds. Such paraffinic compounds are preferably present in an amount in the range of from 0 to 50 wt %, more preferably in the range of from 0 to 40 wt %, still more preferably in the range of from 0 to 30 wt %.

By an olefin is understood an organic compound containing at least two carbon atoms connected by a double bond. The olefin can be a mono-olefin, having one double bond, or a poly-olefin, having two or more double bonds. Preferably olefins present in the olefinic co-feed are mono-olefins. C4 olefins, also referred to as butenes (1-butene, 2-butene, isobutene, and/or butadiene), in particular C4 mono-olefins, are preferred components in the olefinic co-feed.

Preferably the olefinic co-feed is at least partially obtained by a recycle stream formed by recycling a suitable fraction of the reaction product comprising C4 olefin. The skilled artisan knows how to obtain such fractions from the olefinic reaction effluent such as by distillation.

In one embodiment at least 70 wt % of the olefinic co-feed, during normal operation, is formed by the recycle stream, preferably at least 90 wt %, more preferably at least 99 wt %. Most preferably the olefinic co-feed is during normal operation formed by the recycle stream, so that the process converts oxygenate feedstock to predominantly light olefins without the need for an external olefins stream. During normal operation means for example in the course of a continuous operation of the process, for at least 70% of the time on stream. The olefinic co-feed may need to be obtained from an external source, such as from a catalytic cracking unit or from a naphtha cracker, during start-up of the process, when the reaction effluent comprises no or insufficient C4+ olefins.

A particularly preferred olefinic recycle stream is a C4 fraction containing C4 olefin(s), but which can also contain a significant amount of other C4 hydrocarbon species, in particular C4 paraffins, because it is difficult to economically separate C4 olefins and paraffins, such as by distillation.

In a preferred embodiment the olefinic co-feed and preferably also the recycle stream comprises C4 olefins and less than 10 wt % of C5+ hydrocarbon species, more preferably at least 50 wt % of C4 olefins, and at least a total of 70 wt % of C4 hydrocarbon species.

The olefinic co-feed and preferably also the recycle stream, can in particular contain at least a total of 90 wt % of C4 hydrocarbon species. In a preferred embodiment, the olefinic co-feed comprises less than 5 wt % of C5+ olefins, preferably less than 2 wt % of C5+ olefins, even more preferably less than 1 wt % of C5+ olefins, and likewise the recycle stream. In another preferred embodiment, the olefinic co-feed, comprises less than 5 wt % of C5+ hydrocarbon species, preferably less than 2 wt % of C5+ hydrocarbon species even more preferably less than 1 wt % of C5+ hydrocarbon species, and likewise the recycle stream.

Thus in certain preferred embodiments, the olefinic portion of the olefinic co-feed, and of the recycle stream, comprises at least 90 wt % of C4 olefins, more preferably at least 99 wt %. Butenes as co-feed have been found to be particularly beneficial for high ethylene selectivity. Therefore one particularly suitable recycle stream consists essentially, i.e. for at least 99 wt %, of 1-butene, 2-butene (cis and trans), isobutene, n-butane, isobutane, butadiene.

In certain embodiments, the recycle stream can also comprise propylene. This may be preferred when a particularly high production of ethylene is desired, so that part or all of the propylene produced, such as at least 5 wt % thereof, is recycled together with C4 olefins.

The preferred molar ratio of oxygenate in the oxygenate feedstock to olefin in the olefinic co-feed depends on the specific oxygenate used and the number of reactive oxygen-bonded alkyl groups therein. Preferably the molar ratio of oxygenate to olefin in the total feed lies in the range of 10:1 to 1:10, more preferably in the range of 5:1 to 1:5 and still more preferably in the range of 3:1 to 1:3.

In a preferred embodiment wherein the oxygenate comprises only one oxygen-bonded methyl group, such as methanol, the molar ratio preferably lies in the range of from 5:1 to 1:5 and more preferably in the range of 2.5:1 to 1:2.5.

In another preferred embodiment wherein the oxygenate comprises two oxygen-bonded methyl groups, such as for example dimethylether, the molar ratio preferably lies in the range of from 5:2 to 1:10 and more preferably in the range of 2:1 to 1:4. Most preferably the molar ratio in such a case is in the range of 1.5:1 to 1:3.

The process to prepare an olefin is typically carried out in presence of a molecular sieve having one-dimensional 10-membered ring channels. These are understood to be molecular sieves having only 10-membered ring channels in one direction which are not intersected by other 8, 10 or 12-membered ring channels from another direction.

Preferably, the molecular sieve is selected from the group of TON-type (for example zeolite ZSM-22), MTT-type (for example zeolite ZSM-23), STF-type (for example SSZ-35), SFF-type (for example SSZ-44), EUO-type (for example ZSM-50), and EU-2-type molecular sieves or mixtures thereof.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type molecular sieves are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type molecular sieves are more particularly described in e.g. U.S. Pat. No. 4,397,827. For purposes of the present invention, EU-2 is considered to include its isotypes, e.g., ZSM-48.

In a further preferred embodiment a molecular sieve of the MTT-type, such as ZSM-23, and/or a TON-type, such as ZSM-22 is used.

Molecular sieve and zeolite types are for example defined in Ch. Baerlocher and L. B. McCusker, Database of Zeolite Structures: http://www.iza-structure.org/databases/, which database was designed and implemented on behalf of the Structure Commission of the International Zeolite Association (IZA-SC), and based on the data of the 4th edition of the Atlas of Zeolite Structure Types (W. M. Meier, D. H. Olson and Ch. Baerlocher). The *Atlas of Zeolite Framework Types*, 5th revised edition 2001 and 6th edition 2007 may also be consulted.

Preferably, molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 300° C. The molecular sieves obtained after ion-exchange are also referred to as being in the ammonium form.

Preferably the molecular sieve having one-dimensional 10-membered ring channels has a silica to alumina ratio (SAR) in the range of from 1 to 500, preferably in the range of from 10 to 200. The SAR is defined as the molar ratio of $SiO_2/Al_2O_3$ corresponding to the composition of the molecular sieve.

For ZSM-22, a SAR in the range of 40-150 is preferred, in particular in the range of 70-120. Good performance in terms of activity and selectivity has been observed with a SAR of about 100.

For ZSM-23, an SAR in the range of 20-120 is preferred, in particular in the range of 30-80. Good performance in terms of activity and selectivity has been observed with a SAR of about 50.

In a special embodiment the reaction is performed in the presence of a more-dimensional molecular sieve, such as ZSM-5. Suitably to this end the oxygenate conversion catalyst comprises at least 1 wt %, based on total molecular sieve in the oxygenate conversion catalyst, of a further molecular sieve having more-dimensional channels, in particular at least 5 wt %, more in particular at least 8 wt %.

The further molecular sieve having more-dimensional channels is understood to have intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. The further molecular sieve can be for example a FER type zeolite which is a two-dimensional structure and has 8- and 10-membered rings intersecting each other. Preferably however the intersecting channels in the further molecular sieve are each 10-membered ring channels. Thus the further molecular sieve may be a zeolite, or a SAPO-type (silicoaluminophosphate) molecular sieve. More preferably however the further molecular sieve is a zeolite. A preferred further molecular sieve is an MFI-type zeolite, in particular zeolite ZSM-5.

The presence of the further molecular sieve in the oxygenate conversion catalyst was found to improve stability (slower deactivation during extended runs) and hydrothermal stability compared to a catalyst with only the one-dimensional molecular sieve and without the more-dimensional molecular sieve. Without wishing to be bound by a particular hypothesis or theory, it is presently believed that this is due to the possibility for converting larger molecules by the further molecular sieve having more-dimensional channels, that were produced by the first molecular sieve having one-dimensional 10-membered ring channels, and which would otherwise form coke. When the one-dimensional aluminosiclicate and the more-dimensional molecular sieve are formulated such that they are present in the same catalyst particle, such as in a spray-dried particle, this intimate mix was found to improve the selectivity towards ethylene and propylene, more in particular towards ethylene.

The weight ratio between the molecular sieve having one-dimensional 10-membered ring channels, and the further molecular sieve having more-dimensional channels can be in the range of from 1:100 to 100:1, preferably 1:1 to 100:1. Preferably the further molecular sieve is the minority component, i.e. the above weight ratio is 1:1 to 100:1, more preferably in the range of 9:1 to 2:1.

Preferably the further molecular sieve is a MFI-type molecular sieve, in particular zeolite ZSM-5, having a silica to alumina ratio (SAR) of at least 60, more preferably at least 80, even more preferably at least 100, yet more preferably at least 150. At higher SAR the percentage of C4 saturates in the C4 totals produced is minimized. In special embodiments the oxygenate conversion catalyst can comprise less than 35 wt % of the further molecular sieve, based on the total molecular sieve in the oxygenate conversion catalyst, in particular less than 20 wt %, more in particular less than 18 wt %, still more in particular less than 15 wt %.

In one embodiment the oxygenate conversion catalyst can comprise more than 50 wt %, at least 65 wt %, based on total molecular sieve in the oxygenate conversion catalyst, of the molecular sieve having one-dimensional 10-membered ring channels. The presence of a majority of such molecular sieve strongly determines the predominant reaction pathway.

The molecular sieve can be used as such or in a formulation, such as in a mixture or combination with a so-called binder material and/or a filler material, and optionally also with an active matrix component. Other components can also be present in the formulation. If one or more molecular sieves are used as such, in particular when no binder, filler, or active matrix material is used, the molecular sieve itself is/are referred to as oxygenate conversion catalyst. In a formulation, the molecular sieve in combination with the other components of the mixture such as binder and/or filler material is/are referred to as oxygenate conversion catalyst.

It is desirable to provide a catalyst having good mechanical or crush strength, because in an industrial environment the catalyst is often subjected to rough handling, which tends to break down the catalyst into powder-like material. The latter causes problems in the processing. Preferably the molecular sieve is therefore incorporated in a binder material. Examples of suitable materials in a formulation include active and inactive materials and synthetic or naturally occurring zeolites as well as inorganic materials such as clays, silica, alumina, silica-alumina, titania, zirconia and aluminosilicate. For present purposes, inert materials, such as silica, are preferred because they may prevent unwanted side reactions which may take place in case a more acidic material, such as alumina or silica-alumina is used.

In one embodiment the oxygenate added can be used for temperature control, and to this end the temperature of the oxygenate added to at least one of the riser reactors of any one of the riser reactor stages is set in dependence of a predetermined desired temperature in this riser reactor. For example, depending on the temperature and mass flow rate of the effluent stream from the previous riser reactor, the temperature and mass flow rate of additional catalyst, the temperature of the oxygenate can be set, e.g. by heat exchange, so that near the inlet of the riser reactor a predetermined inlet temperature of the mixture of the various feeds is realized.

In one embodiment, each gaseous effluent from one of the riser reactors has an oxygenate concentration below 10 wt %, in particular below 5 wt %, preferably below 2 wt %, more preferably below 1 wt %, still more preferably below 0.1 wt %. In this way, substantially full conversion of oxygenate in each riser reactor is realized. This is particularly beneficial at the last reactor effluent, as otherwise unreacted oxygenate has to be separated from the effluent in a work-up section. Separating e.g. unreacted methanol from water formed in the process is an undesirable and costly step in an industrial process.

The reaction to produce the olefins can be carried out over a wide range of temperatures and pressures. Suitably, however, the oxygenate feed and olefinic co-feed are contacted with the molecular sieve at a temperature in the range of from 200° C. to 650° C. In a further preferred embodiment the temperature is in the range of from 250° C. to 600° C., more preferably in the range of from 300° C. to 550° C., most preferably in the range of from 450° C. to 550° C. Preferably the reaction to produce the olefins is conducted at a temperature of more than 450° C., preferably at a temperature of 460° C. or higher, more preferably at a temperature of 490° C. or higher. At higher temperatures a higher activity and ethylene selectivity is observed. Molecular sieves having one-dimensional 10-membered ring channels can be operated under oxygenate conversion conditions at such high temperatures with acceptable deactivation due to coking, contrary to molecular sieves with smaller pores or channels, such as 8-membered ring channels. Temperatures referred to hereinabove represent reaction temperatures, and it will be understood that a reaction temperature can be an average of temperatures of various feed streams and the catalyst in the reaction zone.

In addition to the oxygenate, and the olefinic co-feed, a diluent may be fed into the reactor system. It is preferred to operate without a diluent, or with a minimum amount of diluent, such as less than 200 wt % of diluent based on the total amount of oxygenate feed, in particular less than 100 wt %, more in particular less than 20 wt %. Any diluent known by the skilled person to be suitable for such purpose can be used. Such diluent can for example be a paraffinic compound or mixture of compounds. Preferably, however, the diluent is an inert gas. The diluent can be argon, nitrogen, and/or steam. Of these, steam is the most preferred diluent. For example, the oxygenate feed and optionally olefinic co-feed can be diluted with steam, for example in the range of from 0.01 to 10 kg steam per kg oxygenate feed. In one embodiment small amounts of water are added in order to improve the stability of the catalyst by reducing coke formation.

In one embodiment, each gaseous effluent from one of the riser reactor stages, or preferably from all riser reactors individually, has a concentration of C5+ olefins (pentenes and higher olefins) of below 10 wt %, preferably below 5 wt %, more preferably below 2 wt %, yet more preferably below 1 wt %, still more preferably below 0.1 wt %. In particular, the C5+ olefins can comprise at least 50 wt % pentenes, more in particular at least 80 wt %, even more in particular at least 90 wt % of pentenes. In particular the pentene concentration of the gaseous effluent can be below 10 wt %, preferably below 5 wt %, more preferably below 2 wt %, yet more preferably below 1 wt %, still more preferably below 0.1 wt %.

In this way the ratio of C5+ olefins (in particular C5 olefins) to oxygenate at the subsequent riser inlet to which oxygenate is added is kept minimum in the process. Without wishing to be bound to a particular hypothesis, it is currently believed that keeping the ratio C5+ olefins/oxygenate, in particular C5 olefins/oxygenate, small is beneficial to ethylene selectivity, more in particular in the case that the oxygenate comprises oxygen-bonded methyl groups. It is currently believed that pentenes should be preferentially cracked to yield ethylene and propylene, as opposed to alkylation to higher olefins by reaction with the oxygenate. Cracking of higher olefins is thought to result is a lower concentration of ethylene in the final product.

The olefinic product or reaction effluent is typically fractionated. The skilled artisan knows how to separate a mixture of hydrocarbons into various fractions, and how to work up fractions further for desired properties and composition for further use. The separations can be carried out by any method known to the skilled person in the art to be suitable for this purpose, for example by vapour-liquid separation (e.g. flashing), distillation, extraction, membrane separation or a combination of such methods. Preferably the separations are carried out by means of distillation. It is within the skill of the artisan to determine the correct conditions in a fractionation column to arrive at such a separation. He may choose the correct conditions based on, inter alia, fractionation temperature, pressure, trays, reflux and reboiler ratios.

At least a light olefinic fraction comprising ethylene and a heavier olefinic fraction comprising C4 olefins and less than 10 wt % of C5+ hydrocarbon species are normally obtained. Preferably also a water-rich fraction is obtained. Also a lighter fraction comprising methane, carbon monoxide, and/or carbon dioxide can be obtained, as well as one or more heavy fractions comprising C5+ hydrocarbons. Such heavy fraction can for example be used as gasoline blending component.

In the process also a significant amount of propylene is normally produced. The propylene can form part of the light olefinic fraction comprising ethene, and which can suitably be further fractionated into various product components. Propylene can also form part of the heavier olefinic fraction comprising C4 olefins. The various fractions and streams referred to herein, in particular the recycle stream, can be obtained by fractionating in various stages, and also by blending streams obtained during the fractionation. Typically, an ethylene and a propylene stream of predetermined purity such as pipeline grade, polymer grade, chemical grade or export quality will be obtained from the process, and also a stream rich in C4 comprising C4 olefins and optionally C4 paraffins. In a preferred embodiment the process according to the invention is designed to produce lower olefins for recovery and onward processing and/or sale. Typically therefore, a stream comprising at least 50 wt %, preferably at least 75 wt %, C2 to C3 olefins (ethylene and/or propylene) is separated from the reaction product, based on total reaction product.

It shall be clear that the heavier olefinic fraction comprising C4 olefins, which can form the recycle stream, can be composed from quantities of various fractionation streams. So, for example, some amount of a propylene-rich stream can be blended into a C4 olefin-rich stream. In a particular embodiment at least 90 wt % of the heavier olefinic fraction comprising C4 olefins can be formed by the overhead stream from a debutaniser column receiving the bottom stream from a depropanizer column at their inlet, more in particular at least 99 wt % or substantially all.

Suitably the olefinic reaction effluent comprises less than 10 wt %, preferably less than 5 wt %, more preferably less than 1 wt %, of C6-C8 aromatics. Producing low amounts of aromatics is desired since any production of aromatics consumes oxygenate which is therefore not converted to lower olefins.

The process may be started up by using olefins obtained from an external source for the olefinic co-feed, if used. Such olefins may for example be obtained from a steam cracker, a catalytic cracker, alkane dehydrogenation (e.g. propane or butane dehydrogenation). Further, such olefins can be bought from the market.

When a molecular sieve having more-dimensional channels such as ZSM-5 is present in the oxygenate conversion catalyst, even in minority compared to the molecular sieve having one-dimensional 10-membered ring channels, start up is possible without an olefinic co-feed from an external source. ZSM-5 for example is able to convert an oxygenate to an olefin-containing product, so that a recycle can be established.

Typically the oxygenate conversion catalyst deactivates in the course of the process. Conventional catalyst regeneration techniques can be employed, such as oxidation of coke in a regenerator. The molecular sieve having one-dimensional 10-membered ring channels used in the process of the present invention can have any shape known to the skilled person to be suitable for this purpose, for it can be present in the form of spray-dried particles, spheres, tablets, rings, extrudates, etc. Extruded catalysts can be applied in various shapes, such as, cylinders and trilobes. Spray-dried particles are preferred.

Embodiments of the present invention will now be described by way of example only and with reference to and as shown in the accompanying drawings, in which:—

Figure 1:
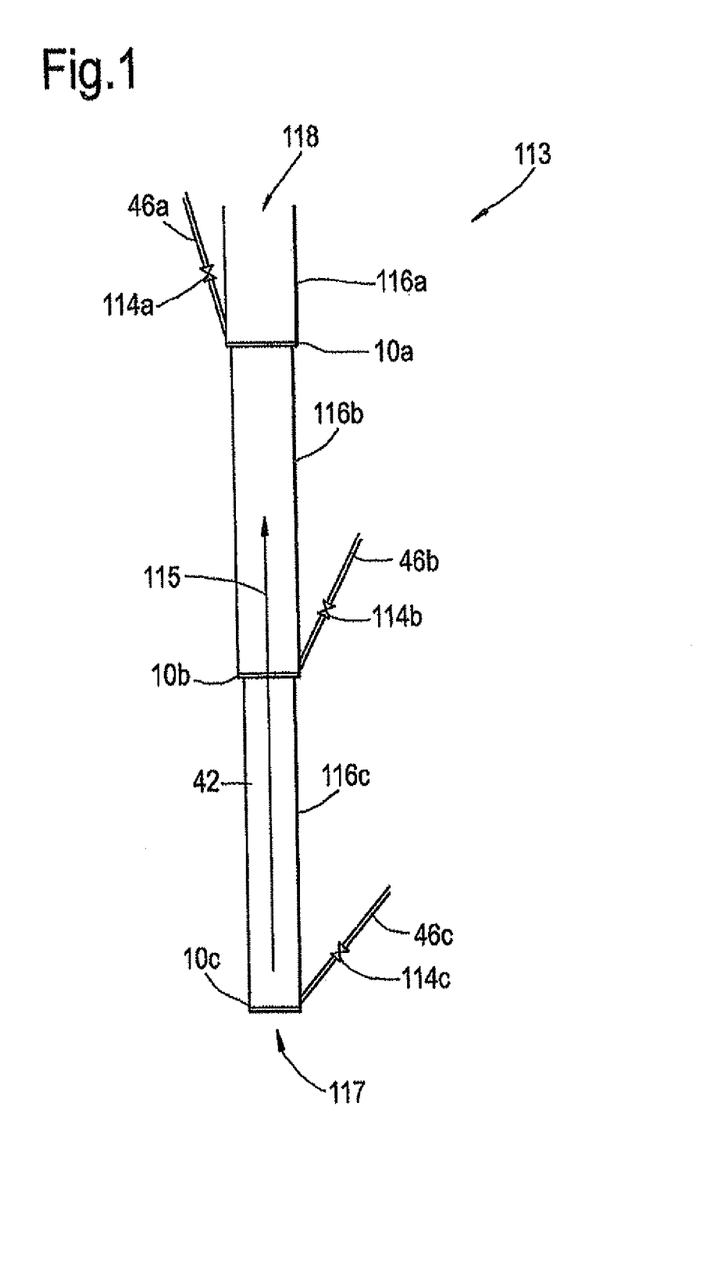
FIG. 1 is a front view of a riser reactor comprising catalyst feed devices in accordance with the present invention.
Figure 2:
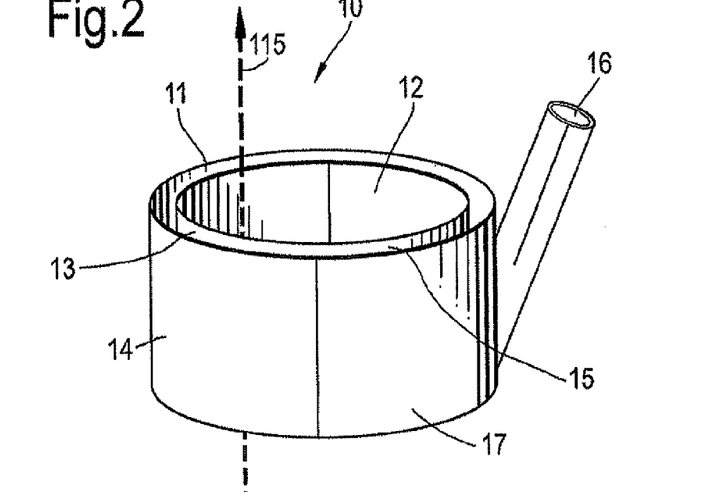
FIG. 2 is a perspective view of a catalyst feed device in accordance with the present invention.
Figure 3:
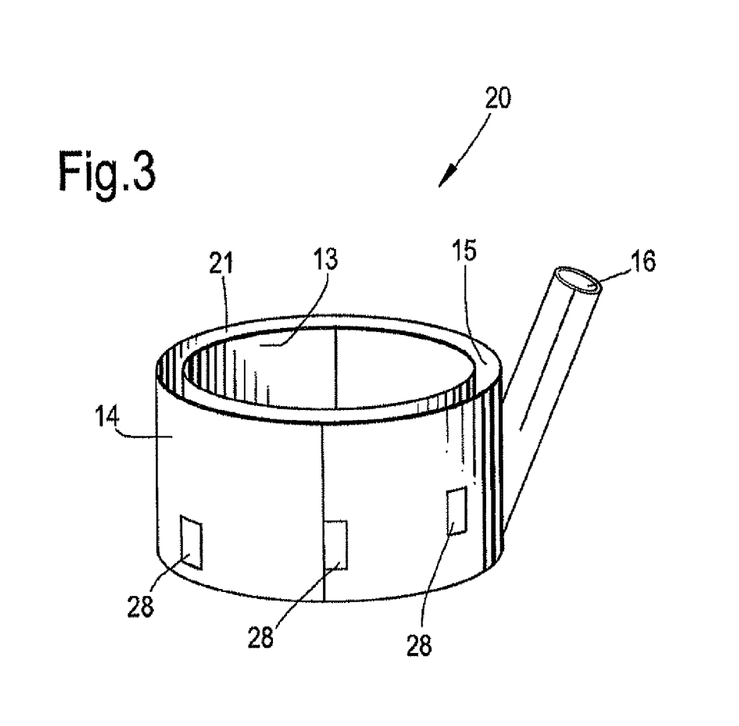
FIG. 3 is a perspective view of a second embodiment of a catalyst feed device in accordance with the present invention.
Figure 4:
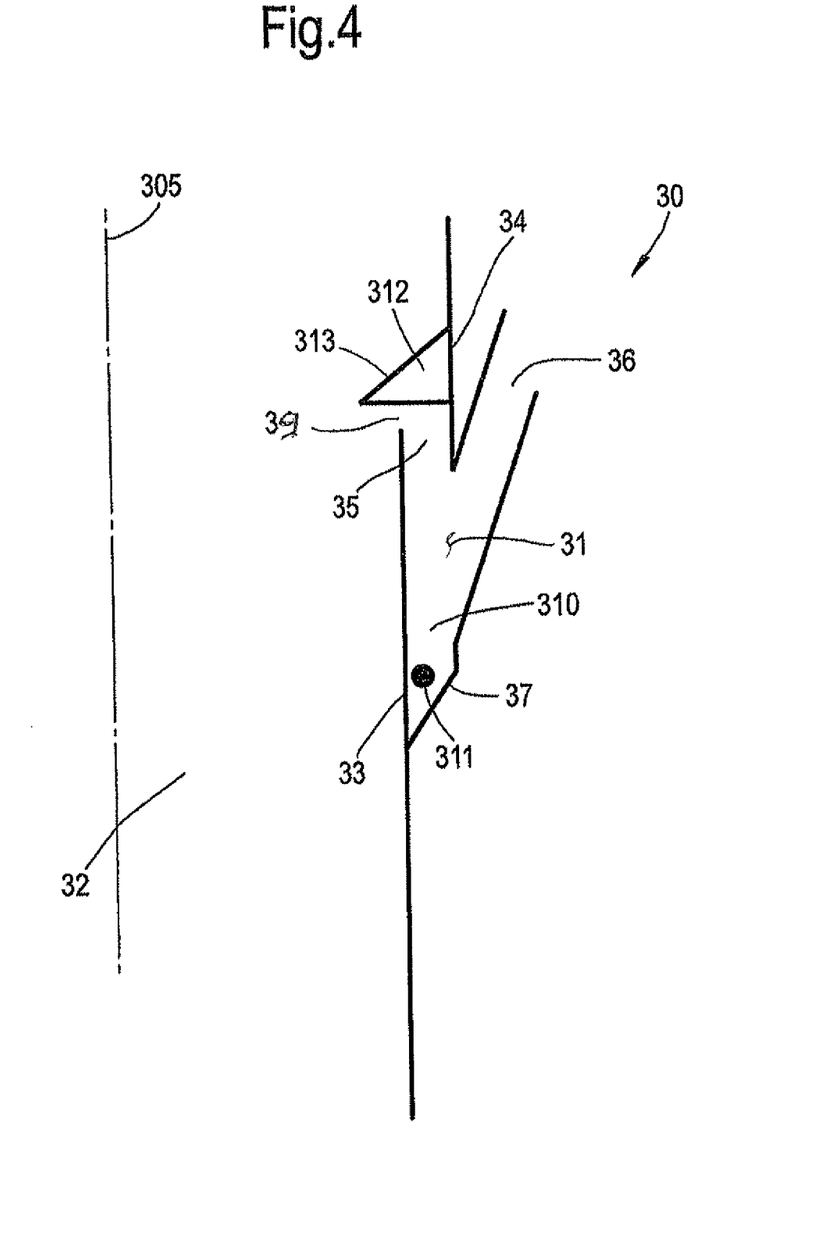
FIG. 4 is a sectional view of a third embodiment of a catalyst feed device in accordance with the present invention.

FIG. 1 is a front view of a riser reactor comprising catalyst feed devices in accordance with the present invention;

FIG. 2 is a perspective view of a catalyst feed device in accordance with the present invention;

FIG. 3 is a perspective view of a second embodiment of a catalyst feed device in accordance with the present invention; and, FIG. 4 is a sectional view of a third embodiment of a catalyst feed device in accordance the present invention.

FIG. 1 shows schematically the riser part of a riser reactor system 113, with catalyst feed devices 10*a*, 10*b* & 10*c* in accordance with the present invention. The riser reactor system 113 of this embodiment comprises three riser segments 116*a*, 116*b* and 116*c*. The riser interior 42 provides a vertical flow path 115 for the catalyst, reactants and products (not shown) from a bottom end 117 to a top end 118 of the riser reactor 113. The catalyst feed devices 10*a*, 10*b* & 10*c* are in fluid communication with upstream standpipes 46*a*, 46*b* & 46*c* from which catalyst is received during operation. Catalyst flow to the feed devices 10*a*, 10*b* & 10*c* can be regulated using respective valves 114*a*, 114*b* and 114*c*, e.g. slide valves.

In one embodiment, the lowest catalyst inlet, equivalent to 10*a*, can also be a conventional catalyst inlet for a riser reactor.

FIG. 2 shows a catalyst feed device 10 (which can be one of 10*a*,*b*,*c*, in FIG. 1) in more detail which in use allows fluidised catalyst to be fed into the riser reactor 113 from around the circumference thereof.

The device 10 comprises an inner wall 13, an outer wall 14 and a base 17; all defining a circumferential trough 15. In a preferred embodiment the outer wall 14 of the catalyst feed device can be part of or an extension of the wall of an upper riser segment and the inner wall 13 can be part of or an extension of the wall of a lower riser segment.

An inlet port 16 connects the trough 15 with one of the ports 46*a*,*b*,*c* shown in FIG. 1 and so provides an upstream opening on one side of the device 10. In use, the upper end of the inner wall 13 functions as a weir over which fluidised catalyst may flow. Thus a downstream opening 11 is provided between an end of the inner wall 13 and the outer wall 14, which extends further upwardly than shown in FIG. 2.

In use, fluidised catalyst is supplied to the device 10 via inlet port 16 and collects in trough 15 before flowing over the inner wall 13 into the reactor and mixing with the flow of fluidised catalyst, reactants and products (not shown) already in the riser interior 12.

An advantage of embodiments of the invention, such as the device 10, is that the fluidised catalyst may be introduced into the riser reactor generally around the circumference thereof, which allows for a more evenly distributed addition of the fluidised catalyst into the riser reactor, compared a situation where fluidised catalyst is added only at one side of a reactor. The present invention thus allows a more even distribution of fluidised components in the reactor rather than biasing the catalyst to one side thereof.

FIG. 3 shows an alternative embodiment of the catalyst feed device 20 with flow distribution baffles 28 provided in the trough 15, the baffles 28 directing fluid toward the top of the inner wall 13 and into the reactor 113. In the drawing it will be understood that the baffles are located in the annular region between riser walls 13 and 14. Three rectangular button-shaped baffles are visible in the drawing at decreasing distance from the base 17 away from the upstream catalyst inlet. It will be understood that the number, orientation, size and shape of the baffles 28 may be varied, in order to optimize the catalyst flow in a particular practical application.

The inventors of the present invention have found that without such baffles or other fluid diverters, fluid flow over the inner wall 13 into the riser reactor can be uneven. For example, at sufficient inflow velocity of catalyst from standpipe 46, the fluidized catalyst can flow around both halves of the trough and be lifted over the weir (upper end of inner wall 13) predominately opposite the inlet port 16. The presence of the baffles 28 can mitigates such an effect, so that part of the catalyst flow is directed over the wear at other locations. In this way a more evenly distributed addition of the fluidised catalyst into the riser reactor 113 can be achieved.

In alternative embodiments, the height of the top edge of inner wall 13 may be uneven, for example it may have a sinusoidal edge or terminate in castellations.

Certain embodiments may also have a plurality of apertures (not shown) in the inner wall 13 through which fluidised catalyst may flow from trough 15 into the riser interior 12, in addition to a flow path over a weir, or in place thereof (in which latter case the trough would be closed at an upper end thereof).

FIG. 4 shows a half-sectional view of a catalyst feed device 30 which shares many features with previous embodiments and reference numerals of such features, 31-37, are preceded by a 3 (instead of a 1) and only described further where needed. Only half of a longitudinal cross-section through a riser reactor system at the location of and a catalyst feed device is shown, line 305 represents the axis of the cylindrical riser geometry.

The outer wall 34 extends vertically above the inner wall 33 and provides support for a shoulder 312. The shoulder 312 prevents ingress of any backflow of fluids from the riser interior 32 into the trough 35. The upper face 313 of shoulder 312 tapers inwards towards the riser interior 32 and downwardly, and so directs any backflow of fluids towards the centre of the reactor 113.

A downstream opening 39 between the shoulder 312 and inner wall 33 provides an exit route for fluidised catalyst 31, and forms an annular inlet into the riser interior 32. A gas inlet schematically shown as 311 is provided to assist in maintaining the catalyst in the trough 35 fluidised.

Thus embodiments of the present invention provide a device which can more evenly add fluidised catalyst into a riser reactor so to distribute the catalyst therein more evenly compared to conventional catalyst feeds.

Any feature of any aspect of any invention or embodiment described herein may be combined with any feature of any aspect of any other invention or embodiment described herein mutatis mutandis.

What is claimed is:

1. A riser reactor system comprising a riser reactor and a catalyst feed device for fluidized catalyst, the riser reactor having a riser interior in which catalyst is flowing during normal operation, and the feed device comprising an annular trough surrounding the riser interior, the annular trough having an upstream opening for receiving fluidized catalyst, and at least one substantially circumferential downstream opening providing fluid communication between the trough and the riser interior, wherein the catalyst feed device comprises an annular shoulder less than 1 m above said trough, the shoulder extending inwards to an equal or greater extent than an inner wall of the trough.

2. A riser reactor system as claimed in claim 1, wherein the catalyst feed device is at least 50 cm from the bottom of the riser reactor.

3. A riser reactor system as claimed in claim 1, wherein at least one flow distribution baffle is provided in the trough, the at least one baffle being shaped or arranged to manipulate flow of fluidised catalyst in the trough.

4. A riser reactor system as claimed in claim 3, wherein a plurality of flow distribution baffles are provided in the trough, the baffles being shaped or arranged to manipulate flow of fluidised catalyst in the trough.

5. A riser reactor system as claimed in claim 3, wherein the at least one baffle is spaced away from said upstream opening, by between 10 to 170°.

6. A riser reactor system as claimed in claim 1, wherein an upper face of the shoulder tapers inwardly and downwardly.

7. A riser reactor system as claimed in claim 1, wherein the trough comprises an inlet for fluidization gas.

8. A riser reactor system as claimed in claim 1, comprising a plurality of stacked riser segments, each segment having a different diameter, such that an outer wall of the catalyst feed device is a continuation of the wider diameter riser segment, and an inner wall of the catalyst feed device is a continuation of the lower diameter riser segment.

9. A riser reactor system as claimed in claim 1, comprising a further catalyst feed device.

10. A riser reactor system comprising a riser reactor and a catalyst feed device for fluidized catalyst, the riser reactor having a riser interior in which catalyst is flowing during normal operation, and the feed device comprising an annular trough surrounding the riser interior, the annular trough having an upstream opening for receiving fluidized catalyst, and at least one substantially circumferential downstream opening providing fluid communication between the trough and the riser interior, the system comprising a plurality of stacked riser segments, each segment having a different diameter, such that an outer wall of the catalyst feed device is a continuation of the wider diameter riser segment, and an inner wall of the catalyst feed device is a continuation of the lower diameter riser segment.

\* \* \* \* \*